(12) United States Patent
Masuda et al.

(10) Patent No.: US 9,480,678 B2
(45) Date of Patent: *Nov. 1, 2016

(54) ANTIFUNGAL PHARMACEUTICAL COMPOSITION

(75) Inventors: Takaaki Masuda, Yokohama (JP); Naoto Nishida, Yokohama (JP); Naoko Kobayashi, Yokohama (JP); Hideaki Sasagawa, Yokohama (JP)

(73) Assignees: POLA PHARMA INC., Shinagawa-ku, Tokyo (JP); NIHON NOHYAKU CO., LTD., Chuo-ku, Tokyo (JP)

( * ) Notice: Subject to any disclaimer, the term of this patent is extended or adjusted under 35 U.S.C. 154(b) by 395 days.

This patent is subject to a terminal disclaimer.

(21) Appl. No.: 12/676,331

(22) PCT Filed: Sep. 5, 2008

(86) PCT No.: PCT/JP2008/066058
§ 371 (c)(1),
(2), (4) Date: Mar. 3, 2010

(87) PCT Pub. No.: WO2009/031644
PCT Pub. Date: Mar. 12, 2009

(65) Prior Publication Data
US 2010/0168200 A1 Jul. 1, 2010

(30) Foreign Application Priority Data
Sep. 5, 2007 (JP) .................. 2007-229617

(51) Int. Cl.
| | | |
|---|---|---|
| A61K 31/385 | (2006.01) | |
| A61K 31/4164 | (2006.01) | |
| A61K 31/4178 | (2006.01) | |
| A61K 9/00 | (2006.01) | |
| A61K 47/10 | (2006.01) | |
| A61K 47/38 | (2006.01) | |

(52) U.S. Cl.
CPC ......... *A61K 31/4178* (2013.01); *A61K 9/0014* (2013.01); *A61K 31/385* (2013.01); *A61K 31/4164* (2013.01); *A61K 47/10* (2013.01); *A61K 47/38* (2013.01)

(58) Field of Classification Search
CPC . A61K 31/41; A61K 31/385; A61K 31/4164
USPC ......................................... 514/397
See application file for complete search history.

(56) References Cited

U.S. PATENT DOCUMENTS

| | | |
|---|---|---|
| 4,267,169 A | 5/1981 | Kamishita et al. |
| 4,636,520 A | 1/1987 | Umio et al. |
| 4,764,381 A | 8/1988 | Bodor et al. |
| 4,935,241 A * | 6/1990 | Saitoh et al. ............. 424/78.07 |
| 5,340,836 A | 8/1994 | Reinhard et al. |
| 5,690,923 A | 11/1997 | DeVringer et al. |
| 5,753,256 A | 5/1998 | Cordes et al. |
| 5,814,305 A | 9/1998 | Laugier et al. |
| 5,962,536 A | 10/1999 | Komer |
| 5,993,787 A | 11/1999 | Sun et al. |
| 6,007,791 A | 12/1999 | Coombes et al. |
| 6,008,256 A | 12/1999 | Haraguchi et al. |
| 6,017,920 A | 1/2000 | Kamishita et al. |
| 6,083,518 A | 7/2000 | Lindahl |
| 6,407,129 B1 * | 6/2002 | Itoh et al. ................ 514/381 |
| 6,428,654 B1 | 8/2002 | Cronan, Jr. et al. |
| 6,585,963 B1 | 7/2003 | Quan et al. |
| 6,740,326 B1 | 5/2004 | Meyer et al. |
| 2003/0017207 A1 | 1/2003 | Lin et al. |
| 2003/0235541 A1 | 12/2003 | Maibach et al. |
| 2004/0208906 A1 | 10/2004 | Tatara et al. |
| 2005/0232879 A1 | 10/2005 | Sasagawa et al. |
| 2006/0140984 A1 | 6/2006 | Tamarkin et al. |
| 2007/0099932 A1 | 5/2007 | Shirouzu et al. |

(Continued)

FOREIGN PATENT DOCUMENTS

| | | |
|---|---|---|
| EP | 0 070 525 | 1/1983 |
| EP | 0 440 298 | 8/1991 |

(Continued)

OTHER PUBLICATIONS

Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.

(Continued)

*Primary Examiner* — Yong Chong
(74) *Attorney, Agent, or Firm* — Knobbe, Martens, Olson & Bear, LLP

(57) ABSTRACT

Disclosed is an antifungal agent for external use, which is characterized by containing a compound represented by the general formula (1), 50 to 95 mass % of an alcohol such as ethanol, 0.1 to 35 mass % of water or the like, and 0.01 to 5 mass % of a cellulose thickening agent. X is a halogen or H.

General formula (1)

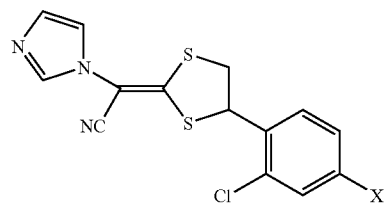

X = a halogen or H

2 Claims, No Drawings

(56) References Cited

U.S. PATENT DOCUMENTS

| | | | |
|---|---|---|---|
| 2008/0021098 A1* | 1/2008 | McGee et al. | 514/462 |
| 2008/0031835 A1 | 2/2008 | Kawamura et al. | |
| 2009/0030059 A1 | 1/2009 | Miki et al. | |
| 2009/0076109 A1 | 3/2009 | Miki et al. | |
| 2009/0099202 A1 | 4/2009 | Shirouzu et al. | |
| 2009/0137651 A1 | 5/2009 | Kobayashi et al. | |
| 2009/0202602 A1 | 8/2009 | Ishima et al. | |
| 2010/0168200 A1 | 7/2010 | Masuda et al. | |
| 2010/0173965 A1 | 7/2010 | Masuda et al. | |
| 2010/0204293 A1 | 8/2010 | Masuda et al. | |
| 2010/0210702 A1 | 8/2010 | Vontz et al. | |
| 2010/0210703 A1 | 8/2010 | Vontz et al. | |
| 2012/0014893 A1 | 1/2012 | Kobayashi et al. | |
| 2012/0022120 A1 | 1/2012 | Kobayashi et al. | |

FOREIGN PATENT DOCUMENTS

| | | |
|---|---|---|
| EP | 0 715 856 | 6/1996 |
| EP | 1 138 314 | 10/2001 |
| EP | 1 522 316 | 4/2005 |
| EP | 1 537 868 | 6/2005 |
| EP | 1 637 132 | 3/2006 |
| EP | 2 005 958 | 12/2008 |
| EP | 2 005 959 | 12/2008 |
| EP | 2 025 337 | 2/2009 |
| EP | 2 191 827 | 6/2010 |
| JP | 61-118315 | 6/1986 |
| JP | 62-093227 | 4/1987 |
| JP | 62-223163 | 10/1987 |
| JP | 01-242525 | 9/1989 |
| JP | 01-242525 A | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-188027 | 7/1995 |
| JP | 07-74144 | 8/1995 |
| JP | 07-206711 | 8/1995 |
| JP | 07-223971 | 8/1995 |
| JP | 08-020527 | 1/1996 |
| JP | 09-100279 | 4/1997 |
| JP | 10-152433 | 6/1998 |
| JP | 10-226639 | 8/1998 |
| JP | 10-226686 | 8/1998 |
| JP | 2001-064206 | 3/2001 |
| JP | 2002-114680 | 4/2002 |
| JP | 3278738 B | 4/2002 |
| JP | 2002-193755 | 7/2002 |
| JP | 2002-284702 | 10/2002 |
| JP | 2002-363070 | 12/2002 |
| JP | 2003-252798 | 9/2003 |
| JP | 2004-529923 | 9/2004 |
| JP | 2005-104924 A | 4/2005 |
| JP | 2005-154306 | 6/2005 |
| JP | 2005-239678 | 9/2005 |
| JP | 2005-289879 | 10/2005 |
| JP | 2006-028123 | 2/2006 |
| JP | 2006-306734 | 11/2006 |
| RU | 2 270 894 C2 | 3/2004 |
| WO | WO 90/14094 | 11/1990 |
| WO | WO 95/30440 | 11/1995 |
| WO | WO 96/11710 | 4/1996 |
| WO | WO 96/40047 | 12/1996 |
| WO | WO 97/02821 | 1/1997 |
| WO | WO 97/07794 | 3/1997 |
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2004/091521 | 10/2004 |
| WO | WO 2005/099764 | 10/2005 |
| WO | WO 2005/123136 | 12/2005 |
| WO | WO 2006/038317 | 4/2006 |
| WO | WO 2007/102242 | 9/2007 |
| WO | WO 2007/077806 | 12/2007 |
| WO | WO 2008/075207 | 6/2008 |
| WO | WO 2010/093992 | 8/2010 |

OTHER PUBLICATIONS

Niwano, et al. "Efficacy of NND-502, A Novel Imidazole Antimycotic Agent, in Experimental Models of *Candida albicans* and *Aspergillus fumigatus* Infections," *International Journal of Antimicrobial Agents*, vol. 12, pp. 221-228, 1999.

Uchida, et al. "In vitro Activity of Novel Imidazole Antifungal Agent NND-502 Against *Malassezia* Species," *International Journal of Antimicrobial Agents*, vol. 21, pp. 234-238, 2003.

Uchida, et al. "In vitro Antifungal Activity of Luliconazole (NND-502), a Novel Imidazole Antifungal Agent," *J Infect Chemother*, vol. 10, pp. 216-219, 2004.

Supplementary European Search Report issued Aug. 12, 2010 to corresponding European application No. 08829675.1.

GHS Classification Guidance for Enterprises ($2^{nd}$ Edition, Ministry of Economy, Trade and Industry, Japan, Mar. 2010.

Crotamiton Properties (http://www.chemspider.com/Chemical-Structure.2780.html) 2 pages.

Absolute ethanol MSDS (www.sciencelab.com/msds.php?msdsld=9923955) 7 pages.

Methyl Ethyl Ketone MSDS (www.sciencelab.com/msds.php?msdsld=9927358) 6 pages.

Niwano, et al. "Lanoconazole and Its Related Optically Active Compound NND-502: Novel Antifungal Imidazoles with a Ketene Dithioacetal Structure," *Current Medicinal Chemistry*, vol. 2, pp. 147-160, 2003.

Martins, et al. "In vitro Sensitivity of Dermatophytes to Urea," *Clinics*, vol. 61, No. 1, pp. 9-14, 2006.

Uchida, et al. "In vitro Antifungal Activity of Luliconazole (NND-502), a Novel Imidazole Antifungal Agent," *Journal of Infectious Chemotherapy*, vol. 10, pp. 216-219, 2004.

Article, "Treatment" in 2 pages downloaded from http://www.babymd.net/dryskin.htm date unknown.

International Search Report dated Nov. 18, 2008 and issued to the priority international application No. PCT/JP2008/066058.

Vieira, et al. "Cationic Lipids and Surfactants as Antifungal Agents: Mode of Action," *Journal of Antimicrobial Chemotherapy*, Vo. 58, pp. 760-767, 2006.

SDS Density downloaded from www.chemicalbook.com/ChemicalProductProperty_EN_CB2147453.htm, 2 pages, copyright 2010.

Pluronics Density downloaded from www.chemicalbook.com/ChemicalProductPropertyEN_CB2709101.htm, 2 pages, copyright 2010.

Ethyl Cellulose Density downloaded from www.chemicalbook.com/ProductMSDSDetailCB6165620_EN.htm 3 pages, copyright 2008.

Niwano, et al. "In vitro and in vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.

Office action issued to related Israeli Patent Application No. 193894 on Oct. 14, 2010 with translation.

Supplemental European Search Report dated Aug. 10, 2010, issued to corresponding European patent application 06811053.5.

Supplementary European Search Report mailed Aug. 16, 2010 and issued to European application No. 06811056.8-2123/2005958.

Examination Report issued Apr. 8, 2010 to corresponding New Zealand Patent Application No. 571818.

International Search Report dated Nov. 18, 2008 issued to international application No. PCT/JP2008/066057.

International Search Report dated Nov. 18, 2008 issued to international application No. PCT/JP2008/066056.

(56) References Cited

OTHER PUBLICATIONS

Supplementary European Search Report issued Aug. 12, 2010 to related European application No. 08829061.4.
Supplementary European Search Report issued Aug. 12, 2010 to related European application No. 08829224.8.
Office Action issued in corresponding European Patent Application No. 08829675.1, mailed on Apr. 19, 2013.
Office Action issued in corresponding Japanese Patent Application No. 2009-531292, mailed on Apr. 23, 2013.

Hoepfner et al., "Fiedler Lexikon der Hilfsstoffe für Pharmazie, Kosmetik und angrenzende Gebiete," ECV Editio Cantor Verlag Aulendorf, pp. [illegible], 1392-1393.
"ICH Harmonised Tripartite Guideline," International Conference on Harmonisation of Technical Requirements for Registration of Pharmaceuticals for Human Use (Jun. 2, 2006).
Luliconazole Pharmaceutical Interview Form (Apr. 2005).
STN search result, Scientific and Technical Information Network (Mar. 14, 1997).

\* cited by examiner

ANTIFUNGAL PHARMACEUTICAL COMPOSITION

CROSS-REFERENCE TO RELATED APPLICATIONS

This application is the U.S. National Phase under 35 U.S.C. §371 of International Application PCT/JP2008/066058, filed Sep. 5, 2008, which was published in a non-English language, which claims priority to JP Application No. 2007-229617, filed Sep. 5, 2007.

TECHNICAL FIELD

The present invention relates to a skin agent for external use, and more specifically, to an antifungal agent for external use.

BACKGROUND ART

Many patients are suffering from diseases such as athlete's foot and candidiasis to be caused by fungi, and the diseases are difficult to be cured completely owing to repeated remissions and relapses. The number of female patients is showing an increasing trend along with women's participation in society in recent years. Thus, there is a social demand for an antifungal agent capable of treating the diseases in a simple manner.

It has been clarified that for a promising antifungal agent, a compound represented by the general formula (1) as a novel imidazole compound having an antifungal activity has an action of shortening a therapeutic period of diseases derived from fungi, and, in particular, luliconazole, which is an optically-active substance, can be exemplified (see JP 3278738 B). Further, such compounds are useful for onychomycosis, and a formulation for onychomycosis thereof is also already known (for example, see WO 03/105841). That is, the compound represented by the general formula (1) may be said to be a useful active ingredient that can be widely used for mycoses (has an antifungal action).

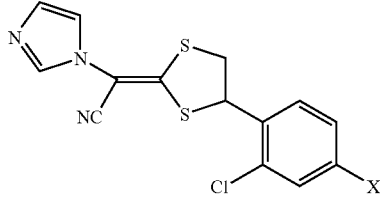

General formula (1)

X = a halogen or H

For mycoses, there are exemplified, in addition to visceral mycoses, mycoses to be caused by the growth of fungi on the skin such as tinea pedis, tinea corporis, tinea cruris, intertrigo, erosio interdigitalis blastomycetica, chromophytosis, and seborrheic dermatitis. In those diseases, it is desired that an antifungal agent for external use be directly applied to a disease site.

Further, in many antifungal agents, adverse effects such as hepatic dysfunction and renal dysfunction due to oral administration are observed in a certain percentage. In addition, in the case of oral administration, a drug is metabolized in the liver and the like by a first-pass effect and the like. Hence, the drug is administered in a large amount for the purpose of delivering the drug to a disease site at an effective concentration, resulting in a burden on organs such liver involved in metabolism. Accordingly, in the current aging society, the utilization of an antifungal agent for external use capable of avoiding the first-pass in the liver has a significant meaning in medical care because the antifungal agent places a small burden on an elderly person in weak physical condition and can be easily administrated.

Meanwhile, because the steric structure of a compound having an asymmetric carbon is unstable in a solution, the maintenance of the steric structure becomes a critical issue in addition to the solubility in the compound having an asymmetric carbon out of bulk drugs for antifungal agents, and thus, various studies are being conducted. This is because the steric structure may be easily changed in a dissolution state. Any of the addition of sugars (see JP 2000-169372 A) and the adjustment of a pH (see JP 06-065076 A) has been conducted as one measure for the above, for example. In addition, it is known that an imidazole derivative is easily dissolved by polyethylene glycol, to thereby provide satisfactory stability (see JP 05-070351 A). However, there is no definite law for maintenance property of such steric structure. Thus, it may be said that the case where the steric structure may be maintained is rare in itself. Further, such combination is incidentally found out under the present situation. In a formulation containing the compound represented by the general formula (1), there has been no finding about whether or not the maintenance of the steric structure of the compound becomes a problem, and further, it is not known how to achieve such maintenance of the steric structure. Under such backgrounds, in pharmaceutical administration and regulations, there is a demand for means for ensuring the stability suited for the compound represented by the general formula (1). In addition, an alcohol typified by ethanol and water are widely used medium ingredients in formulation. It is known that those ingredients may cause hydrolysis or the like to affect the stability of an active ingredient. However, there has been no finding that the ingredients have a preferred contribution to the stability in a specified mixing ratio.

Further, seborrheic dermatitis is exemplified as one of mycoses to which a skin agent for external use is suitable applied. However, a formulation used for seborrheic dermatitis is applied to a scalp site around the hair, and thus is used in a larger amount compared with that used for mycoses of the body and mycoses of the hands and feet. Therefore, the use of a solvent such as methyl ethyl ketone is restricted from the viewpoints of possibility of causing an irritation, flammability, and the like. Accordingly, there has been a demand for a formulation that is free of any adverse effect such as an irritation and can be easily administered. In addition, in order to ensure an effect, preferred is a form of a single-phase solution in which a drug is sufficiently dissolved in a formulation, and a drug is easily transferred to the skin. Because the compound represented by the general formula (1) is limited water solubility, one problem is how to prepare a formulation in a form of a single-phase solution without impairing the solubility.

In the case of developing a skin agent for external use to be used in medical care, a technology for allowing an active ingredient to be sufficiently absorbed in the skin is required as the most important technology. The skin has a defensive action against physical and chemical irritations from the outside. Thus, in general, the absorption amount of an active ingredient from the skin is slight. In order to overcome the problem, a method of improving the transdermal absorbability by various methods has been studied, and a method using a transdermal absorption promoter has been studied, for example (see JP 08-3070 A). For a method of improving the transdermal absorbability of an antifungal skin agent for external use, it has been known that the incorporation of ethylcellulose, water, and a plasticizer in a certain amount allows the antifungal skin agent for external use to be efficiently absorbed (see JP 07-223971 A). However, there is no finding on an effective method of improving the transdermal absorbability to develop the compound represented by the general formula (1) as the antifungal agent for external use. In particular, a method of maintaining the steric structure of the compound in a stable manner and improving the transdermal absorbability has not been studied in any way.

DISCLOSURE OF THE INVENTION

Problem to be Solved by the Invention

The present invention has been made under such circumstances. An object of the present invention is to provide a formulation in which the steric structure of a compound represented by the general formula (1) is maintained in a stable state, and the transdermal absorbability is improved.

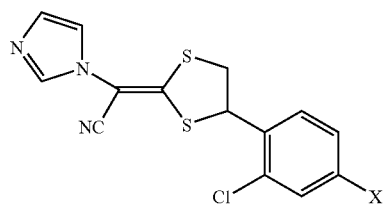

General formula (1)

X = a halogen or H

Means for Solving the Problem

The inventors of the present invention have intensively studied to search a method that can improve the transdermal absorbability of a skin agent for external use containing the compound represented by the general formula (1) and maintain the steric structure of the compound. As a result, the inventors have found that, in a formulation of the compound represented by the general formula (1), the stability of such steric structure is improved by dissolving the compound represented by the general formula (1) in an alcohol such as ethanol, and adding a specified proportion of water. The inventors have also found that the transdermal absorbability is improved while the steric structure is maintained by incorporating a cellulose-based thickener in a certain proportion. For the mass ratio of the alcohol such as ethanol, water, and cellulose-based thickener as described above with respect to the total amount of the formulation, the alcohol such as ethanol is in a range of 50 to 95 mass %, while water is 0.1 to 35 mass % and the cellulose-based thickener is 0.01 to 5 mass %. It should be noted that such formulation system may be adopted without any particular limitation as long as the system is a dosage form generally used for a skin medicine for external use. However, a form of a single-phase solution is preferred.

Based on such finding, the inventors of the present invention have completed the present invention. That is, the present invention is as follows:

(1) an antifungal agent for external use, containing: 1) a compound represented by the general formula (1); 2) 50 to 95 mass % of an alcohol; 3) 0.1 to 35 mass % of water and/or an anionic surfactant; and 4) 0.01 to 5 mass % of a cellulose-based thickener;

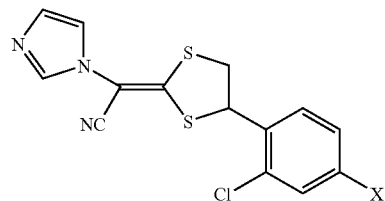

General formula (1)

X = a halogen or H (2) the antifungal agent for external use according to the item (1), in which the compound represented by the general formula (1) is luliconazole;

(3) the antifungal agent for external use according to the item (1) or (2), containing 1 mass % or less of a flammable solvent excluding an alcohol with respect to a total amount of the antifungal agent for external use;

(4) the antifungal agent for external use according to any one of the items (1) to (3), in which the antifungal agent is in a form of a single-phase solution;

(5) the antifungal agent for external use according to any one of the items (1) to (4), in which a disease to which the antifungal agent is applied is selected from the group consisting of tinea (tinea pedis, tinea corporis, or tinea cruris), candidiasis (intertrigo or erosio interdigitalis blastomycetica), chromophytosis, and seborrheic dermatitis; and (6) the antifungal agent for external use according to the item (5), in which the disease to which the antifungal agent is applied is seborrheic dermatitis.

Effects of the Invention

According to the present invention, there can be provided a formulation with safety and high transdermal absorbability containing the compound represented by the general formula (1). Such formulation is applicable to mycoses such as tinea (tinea pedis, tinea corporis, or tinea cruris), candidiasis (intertrigo or erosio interdigitalis blastomycetica), chromophytosis, or seborrheic dermatitis, and may be usefully used for, in particular, seborrheic dermatitis.

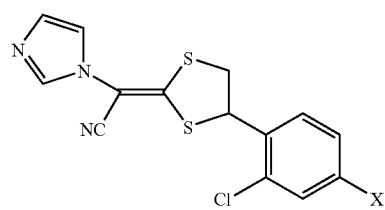

General formula (1)

X = a halogen or H

BEST MODE FOR CARRYING OUT THE INVENTION

An antifungal agent for external use of the present invention contains a compound represented by the general formula (1), 50 to 95 mass % of an alcohol such as ethanol, 0.1 to 35 mass % of water, and 0.01 to 5 mass % of a cellulose-based thickener. Part or all of water may be replaced by an anionic surfactant.

When X in the compound represented by the general formula (1) represents a halogen, preferred examples of the halogen include chlorine, bromine, iodine, and fluorine. Of those, chlorine is preferred.

Further, the content of the compound represented by the general formula (1) is preferably 0.01 to 20 mass % and particularly preferably 0.1 to 10 mass % with respect to the total amount of an antifungal agent for external use.

An alcohol typified by ethanol dissolves the compound, and hence is incorporated in an amount of preferably 50 to 95 mass % and further, more preferably 70 to 90 mass % with respect to the total amount of the above antifungal agent for external use. This is because the compound may not be sufficiently dissolved and may be time-dependently precipitated when an alcohol content is small. Ethanol is preferred as the alcohol to be used in the present invention. However, other alcohols used for a skin agent for external use may also be used in place of ethanol. Further, alcohols which may be mixed with water at an arbitrary ratio are preferred as alcohols other than ethanol, and specific suitable examples include polyvalent alcohols such as propylene glycol, 1,3-butanediol, glycerin, and polypropylene glycol. When such alcohols other than ethanol are used, it is particularly preferred to use those alcohols other than ethanol in such a form that a part of ethanol is replaced by one kind or two or more kinds selected from the alcohols other than ethanol. In this case, it is preferred that ethanol be not less than 50 mass % with respect to the total amount of the alcohols. The above-mentioned amount is particularly preferred in order to exhibit a form of a single-phase solution. In contrast, an excess alcohol amount may impair the degree of freedom in prescription. Further, the addition of water may suppress a time-dependent change of the compound in a formulation, for example, a change of the compound into a compound having a changed steric structure such as an S-E isomer represented by the general formula (2) and a Z isomer represented by the general formula (3), in particular, a change of the compound into the S-E isomer. In order to obtain the effect, the amount of water is preferably 0.1 to 35 mass % and more preferably 1 to 30 mass % with respect to the total mass of the antifungal agent for external use. In the case of using the formulation as a gel formulation by incorporating other aqueous thickeners other than cellulose-based one and the like, the percentage of water is, for example, preferably 5 to 35 mass % and more preferably 10 to 30 mass % with respect to the total weight of the antifungal agent for external use. For ingredients for improving the stability of the steric structure of the compound represented by the general formula (1) as described above, there are given anionic surfactants such as sodium dodecyl sulfate and sodium polyoxyethylene (4) lauryl ether phosphate in addition to water, and such ingredients may also be used in place of water. However, in the invention of the present application, it is preferred to use only water without using such ingredients because such ingredients may express an irritation in portions other than the nail. Further, an emulsifying formulation may also be adopted in the skin agent for external use of the present invention. However, in order to take advantage of good skin permeability due to the use of an alcohol such as ethanol as a solvent, it is preferred that the antifungal agent for external use of the present invention be in a form of a single-phase solution. It should be noted that the term "single-phase solution" as used herein refers to liquid substances dissolved with each other in which no white turbidity is observed and neither liquid crystal nor fine crystal is observed under a polarized light.

In the antifungal agent for external use according to the invention of the present application, the content ratio of water to the alcohol such as ethanol is preferably 1:99 to 4:6, more preferably 5:95 to 3:7, and particularly preferably 1:7 to 3:4 at a mass ratio. Further, when an anionic surfactant is incorporated into the antifungal agent for external use according to the invention of the present application, the preferred content ratio of the anionic surfactant to the alcohol is preferably 1:99 to 4:6. Further, when water and an anionic surfactant are incorporated into the antifungal agent for external use according to the invention of the present application, the water and the anionic surfactant are incorporated so that the ratio of the water to the anionic surfactant comes to preferably 20:1 to 1:1.

Further, as a subsidiary effect, the formulation may be performed without using any flammable hazardous material (first class petroleum) such as methyl ethyl ketone. A form free of any flammable hazardous material is more preferred because the versatility is enhanced owing to such form. In addition, the addition of the cellulose-based thickener can improve the transdermal absorbability while maintaining the steric structure in a stable state. For the cellulose-based thickener that provides such effect, there may be suitably exemplified hydroxypropylmethylcellulose and hydroxypropylcellulose. The amount of the cellulose-based thickener is preferably 0.01 to 5 mass % with respect to the total amount of the above-mentioned antifungal agent for external use and is more preferably 0.1 to 2.5 mass % in order to ensure a form of a single-phase solution. When the content of the cellulose-based thickener is less than 0.01 mass %, an effect of improving the transdermal absorbability cannot be expected, and when the content is more than 5 mass %, a formulation unsuited for a wide range of applications is obtained because the formulation has too high viscosity.

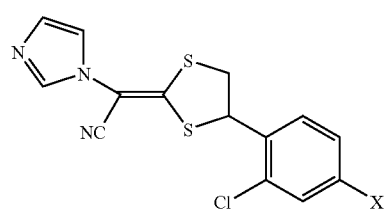

General formula (1)

X = a halogen or H

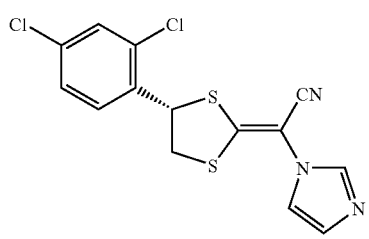

General formula (2)

-continued

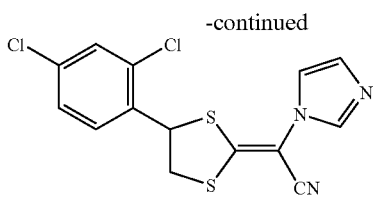

The antifungal agent for external use of the present invention may contain, apart from the above ingredients, an arbitrary ingredient generally used for a skin agent for external use. Favorable examples of the arbitrary ingredient include: oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, hydrogenated coconut oil, hydrogenated oil, Japan wax, hydrogenated castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as oleyl alcohol, cetyl alcohol, stearyl alcohol, isostearyl alcohol, behenyl alcohol, octyldodecanol, myristyl alcohol, and cetostearyl alcohol; synthetic ester oils such as cetylisoctanoate, isopropyl myristate, hexyldecyl isostearate, diisopropyl adipate, diethyl sebacate, diisopropyl sebacate, di-2-ethylhexyl sebacate, hexacetyl lactate, diisostearyl malate, ethylene glycol di-2-ethyl hexanoate, neopentylglycol dicaprate, di-2-heptyl undecanoic acid glyceride, tri-2-ethylhexanoic acid glyceride, trimethylolpropane tri-2-ethylhexanoate, trimethylolpropane triisostearate, and pentane erythrite tetra-2-ethylhexanoate; oil solutions of silicone oil and the like, which are not classified into the above-mentioned silicons, such as modified polysiloxanes including amino-modified polysiloxane, polyether-modified polysiloxane, alkyl-modified polysiloxane, and fluorine-modified polysiloxane; anionic surfactants such as fatty acid soaps (such as sodium laurate and sodium palmitate), potassium lauryl sulfate, triethanolamine alkyl sulfate ether, and sodium polyoxyethylene lauryl phosphate; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazoliniumhydroxide-1-carboxyethyloxy-2-sodium salt), betaine-based surfactants (such as alkyl betaine, amide betaine, and sulfo betaine), and acylmethyl taurine; nonionic surfactants such as sorbitan fatty acid esters (such as sorbitan monostearate, sorbitan monolaurate, and sorbitan sesquioleate), glycerin fatty acids (such as glycerin monostearate), propyleneglycol fatty acid esters (such as propyleneglycol monostearate), hydrogenated castor oil derivatives, glycerol alkyl ether, POE sorbitan fatty acid esters (such as POE sorbitan monooleate, polyoxyethylene sorbitan monostearate, and polyoxyethylene sorbitan monolaurate), POE sorbitol fatty acid esters (such as POE-sorbitol monolaurate), POE glycerol fatty acid esters (such as POE-glyceryl monoisostearate), POE fatty acid esters (such as polyethyleneglycol monooleate and POE distearate), POE alkyl ethers (such as POE lauryl ether, POE oleyl ether, and POE 2-octyldodecyl ether), POE alkyl phenyl ethers (such as POE octylphenyl ether and POE nonylphenyl ether), pluronic types, POE/POP alkyl ethers (such as POE/POP 2-decyltetradecyl ether), tetronic types, POE castor oil/hydrogenated castor oil derivatives (such as POE castor oil and POE hydrogenated castor oil), sucrose fatty acid ester, and alkyl glycoside; moisturizing ingredients such as sodium pyrrolidone carboxylate, lactic acid, and sodium lactate; pH adjusters such as phosphoric acid and citric acid; powders such as mica, talc, kaolin, synthetic mica, and barium sulfate, whose surfaces may be treated; inorganic pigments such as colcothar, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic powders such as a polyethylene powder, polymethyl methacrylate, a nylon powder, and an organopolysiloxane elastomer; a p-aminobenzoate-based ultraviolet absorbent; an anthranilate-based ultraviolet absorbent; a salicylate-based ultraviolet absorbent; a cinnamate-based ultraviolet absorbent; a benzophenone-based ultraviolet absorbent; a sugar-based ultraviolet absorbent; ultraviolet absorbents such as 2-(2'-hydroxy-5'-t-octylphenyl)benzotriazole and 4-methoxy-4'-t-butyldibenzoylmethane; lower alcohols such as ethanol and isopropanol; vitamins such as vitamin A and derivatives thereof, vitamin Bs such as vitamin $B_6$ hydrochloride, vitamin $B_6$ tripalmitate, vitamin $B_6$ dioctanoate, vitamin $B_2$ and derivatives thereof, vitamin $B_{12}$, and vitamin $B_{15}$ and derivatives thereof, vitamin Es such as α-tocopherol, β-tocopherol, γ-tocopherol, and vitamin E acetate, vitamin Ds, vitamin H, pantothenic acid, pantethine, and pyrroloquinoline quinone; and solvents such as benzyl alcohol, triacetin, crotamiton, carbonic diesters such as prolene carbonate, and ethylene glycol salicylate. When the antifungal agent for external use of the present invention is applied to seborrheic dermatitis, the antifungal agent preferably has an appropriate viscosity for the purpose of preventing a medicament from being dissipated by dripping to sites other than the applied site. To this end, it is preferred to incorporate a cellulose-based thickener as an essential ingredient such as carboxymethylcellulose, hydroxypropylcellulose, hydroxypropylmethylcellulose, and ethylcellulose, and incorporate, as required, a gelling agent such as a methyl vinyl ether-maleic anhydride copolymer, an acrylic resin alkanolamine solution, polyvinylpyrrolidone, and a carboxyvinyl polymer which may be modified with an alkyl group.

In the case of adding, in addition to such cellulose-based thickener, a gelling agent other than the cellulose-based thickener, the cellulose-based thickener and the gelling agent other than the cellulose-based thickener are incorporated so that the total amount comes to preferably 0.05 to 4 mass % and more preferably 0.1 to 4 mass % with respect to the total amount of the antifungal agent for external use. In such aspect, from the viewpoint of an action of promoting the transdermal absorption, the amount of the cellulose-based thickener falls within a range of preferably 0.01 to 5 mass % and more preferably 0.1 to 2.5 mass % with respect to the total amount of the antifungal agent for external use. This is because, when the amount is too small, an effect of preventing dripping may not be exerted, and when the content is too large, a form of a single-phase solution as a preferred form according to the invention of the present application may be impaired, or the antifungal agent for external use may not be delivered to target tissues as pores of the skin owing to too high gel strength.

Further, in the antifungal agent for external use of the present invention, a flammable solvent such as methyl ethyl ketone and N-methyl-2-pyrrolidone excluding an alcohol typified by ethanol out of solvents may be incorporated. It is preferred to incorporate the flammable solvent in an amount of 1 mass % or less with respect to the total amount of the antifungal agent for external use, and it is more preferred to incorporate substantially no flammable solvent. This is because, even if such solvent does not exist, a form of a single-phase solution may be achieved in the construction of the antifungal agent for external use of the invention of the present application, and negative factors such as possibility of causing an irritation and flammability possessed by the solvent may be eliminated. The term "flammable solvent" as used herein refers to special flammables and first class petroleum designated under the Fire Defense Law.

The antifungal agent for external use of the present invention may be produced by treating the above-mentioned essential ingredient, preferred ingredient, arbitrary ingredient, and the like in accordance with a conventional method, and for example, is preferably produced by such procedure as shown in the following examples. The antifungal agent for external use of the present invention produced as described above is applied to, for example, cosmetics involving quasi drugs, skin pharmaceutical compositions for external use, and skin goods for external use, and is particularly preferably applied to antifungal skin medicines for external use. The antifungal agent for external use is preferably applied to skin medicines for seborrheic dermatitis for external use that are applied to a wide range of sites and are administered to sites sensitive to an irritation because the properties of the antifungal agent may be highly utilized. However, the antifungal agent for external use may also be effectively applied to mycoses of the body such as tinea corporis, mycoses of the hands and feet such as tinea pedis, and onychomycosis such as tinea unguium, and hence, the application of the antifungal agent to such mycoses also falls within the technical scope of the present invention.

Hereinafter, the present invention is described in more detail by way of examples. However, it goes without saying that the present invention is not limited to only such examples.

Example 1

Prescription

Luliconazole was dissolved by adding an appropriate amount of ethanol. To the resulting solution, hydroxypropylcellulose ("HPC-H"; manufactured by Nippon Soda Co., Ltd.) was gradually added, water was further added, and homogenization was performed (Table 1). The resultant was defined as Skin agent A for external use. A product obtained by reducing the amount of hydroxypropylcellulose in Skin agent A for external use to 1.5 mass %, and replacing the reduced hydroxypropylcellulose by ethanol was defined as Skin agent B for external use. A solution as a control was prepared by adding only ethanol to 1.2 mass % of luliconazole, and the solution was defined as Skin agent C for external use.

TABLE 1

| Prescription of Skin agent A for external use | |
|---|---|
| Ingredient | mass % |
| Luliconazole | 1.2 |
| Hydroxypropylcellulose | 1.8 |
| Water | 23.7 |
| Ethanol | 73.3 |
| Total | 100 |

Form of formulations: a form of a single-phase and homogeneously dissolved solution was confirmed through a visual check.

No irritating sensation of the formulation was confirmed.

Transdermal Absorption Test

To a plantar part of an isolated guinea pig hind leg, the skin agent for external use was applied, and the whole was left to stand at room temperature for 2 hours. After that, the skin agent for external use was wiped out from the applied site, and further, the applied site was subjected to 5 times of tape stripping with a cellophane tape. After a certain time, the plantar part was excised, the horny cell layer was peeled off, formed into a piece having a certain size, and evaporated to dryness under reduced pressure for 24 hours. To the obtained dried product, methanol was added, luliconazole as a measurement target was extracted in an ultrasonic homogenizer, and filtered through a filter. After that, the concentration of luliconazole in the horny cell layer was measured under the following analysis conditions.

TABLE 2

| Analysis conditions | |
|---|---|
| HPLC condition | |
| Column | Wakosil II 5C18HG, 4.6 × 250 mm, 5 μm (Wako Pure Chemical Industries, Ltd.) |
| Mobile phase | 5 mmol/l formic acid aqueous solution-methanol (20:80, v/v) |
| Flow rate | 1.0 mL/min |
| Split ratio | ca. 2:8 (MS/MS:drain) |
| Injection amount | 2 μL |
| Column temperature | 45° C. |
| Sample temperature | 5° C. |

| MS/MS condition | | | |
|---|---|---|---|
| ESI, positive ion mode | | | |
| Ionization method | Compound | MS 1 (m/z) | MS 2 (m/z) |
| Measured ion | Luliconazole | 354 | 150 |

Measurement instrument: LC-MS-MS (manufactured by Micromass Limited)

The concentration in the horny cell layer is as follows, and it was revealed that the addition of hydroxypropylcellulose increased the concentration of luliconazole in the horny cell layer, and improved the transdermal absorbability. In addition, it was also revealed that, when the content of hydroxypropylcellulose was increased from 1.5 mass % to 1.8 mass, the transdermal absorption amount was increased.

TABLE 3

Concentration in horny cell layer

| Formulation name | Concentration of luliconazole in horny cell layer (μg/cm$^2$) |
|---|---|
| Skin agent A for external use | 0.950 |
| Skin agent B for external use | 0.577 |
| Skin agent C for external use | 0.221 |

Example 2

Prescription

Luliconazole was dissolved by adding an appropriate amount of ethanol. To the resulting solution, hydroxypropylmethylcellulose 2910 ("METOLOSE 60SH-4000"; manufactured by Shin-Etsu Chemical Co., Ltd.) was gradually added, water was further added, and homogenization was performed (Table 4). The resultant was defined as Skin agent D for external use. A solution as a control was prepared by adding only ethanol to 1.2 mass % of luliconazole, and the solution was defined as Skin agent E for external use.

TABLE 4

Prescription of Skin agent D for external use

| Ingredient | mass % |
|---|---|
| Luliconazole | 1.2 |
| Hydroxypropylmethylcellulose 2910 | 1.2 |
| Water | 23.6 |
| Ethanol | 74 |
| Total | 100 |

Form of formulation: a form of a single-phase and homogeneously dissolved solution was confirmed through a visual check.

No irritating sensation of the formulation was confirmed.

The concentration in the horny cell layer is as follows, and it was revealed that the addition of hydroxypropylmethylcellulose 2910 increased the concentration of luliconazole in the horny cell layer, and improved the transdermal absorbability.

TABLE 5

Concentration in horny cell layer

| Formulation name | Concentration of luliconazole in horny cell layer (μg/cm$^2$) |
|---|---|
| Skin agent D for external use | 0.845 |
| Skin agent E for external use | 0.221 |

INDUSTRIAL APPLICABILITY

By compounding the compound represented by the general formula (1), and the alcohol such as ethanol, the water and the like, and the cellulose-based thickener each in an amount within a certain range, the stability of the steric structure of the compound can be maintained, and the absorbability to the skin can be improved.

What is claimed is:

1. An antifungal nail or skin composition for external use, consisting of: 1) about 1.2 mass % of luliconazole represented by the following formula; 2) about 70 to 90 mass % of ethanol; 3) about 1 to 30 mass % of water; and 4) 0.01 to 5 mass % of a cellulose-based thickener selected from hydroxypropylmethylcellulose and hydroxypropylcellulose;

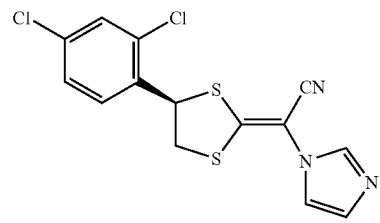 [SMILES: N#C/C(=C1/SC[C@@H](c2ccc(Cl)cc2Cl)S1)n1ccnc1]

luliconazole.

2. The antifungal agent nail or skin composition for external use according to claim 1, wherein the antifungal composition is in a form of a single-phase solution.

* * * * *